United States Patent [19]
Robl

[11] Patent Number: 5,202,327
[45] Date of Patent: Apr. 13, 1993

[54] PHOSPHORUS-CONTAINING HMG-COA REDUCTASE INHIBITORS

[75] Inventor: Jeffrey A. Robl, Holland, Pa.

[73] Assignee: E. R. Squibb & Sons, Inc., Princeton, N.J.

[21] Appl. No.: 727,788

[22] Filed: Jul. 10, 1991

[51] Int. Cl.$^5$ .................. A61K 31/505; C07F 9/02
[52] U.S. Cl. .................. 514/256; 514/274; 544/243
[58] Field of Search .................. 544/243; 514/256, 274

[56] References Cited

U.S. PATENT DOCUMENTS 4,904,646 2/1990 Karanewsky et al. .............. 514/120
4,925,852 5/1990 Kesseler et al. .................. 514/333

OTHER PUBLICATIONS

Karanewsky, et al.; Phosphorus-Containing Inhibitors of HMG-CoA Reductase. 1. 4-[2-Arylethyl)Hydroxyphosphinyl]-3-Hydroxybutanoic Acids: A New Class of Cell-Selective Inhibitors of Cholesterol Biosynthesis. J. Med. Chem. v. 33, no. 11, p. 2952, 1990.

Relationahip Between Tissue Selectivity and Lipophilicity for Inhibitors of HMG-CoA Reductase, Roth, et al.; J. Med. Chem. v. 34, pp. 463-466, 1991.

Primary Examiner—Mukund J. Shah
Assistant Examiner—Y. N. Gupta
Attorney, Agent, or Firm—Suzanne E. Babajko

[57] ABSTRACT

Novel phosphorus-containing compounds which inhibit the activity of HMG-CoA reductase, including a 5-pyrimidinyl-containing moiety. Pharmaceutical compositions and methods of use for the treatment or prevention of hypercholesterolemia, atheroschlerosis, hyperlipoproteinaemia and hyperlipidemia are provided.

18 Claims, No Drawings

PHOSPHORUS-CONTAINING HMG-COA REDUCTASE INHIBITORS

FIELD OF THE INVENTION

The present invention relates to new phosphorus-containing compounds which inhibit the activity of 3-hydroxy-3-methylglutaryl-coenzyme A (HMG-CoA) reductase and thus are useful in inhibiting cholesterol biosynthesis, to pharmaceutical compositions containing such compounds, to new intermediates formed in the preparation of such compounds, and to methods of using such compounds.

BACKGROUND OF THE INVENTION

British Patent No. 2,205,838 discloses HMG-CoA reductase inhibitors which have the formula:

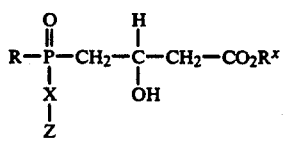

wherein
R is OH or lower alkoxy;
$R^x$ is H or lower alkyl;
X is $-CH_2-$, $-CH_2CH_2-$, $-CH_2CH_2CH_2-$, $-CH=CH-$, $-C\equiv C-$, or $-CH_2O-$ (where O is linked to Z); and
Z is a hydrophobic anchor.

British Patent No. 2,205,837 discloses HMG-CoA reductase inhibitors which have the formula:

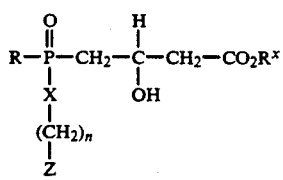

wherein
R is OH, lower alkoxy or lower alkyl;
$R^x$ is H or alkyl;
X is $-O-$ or $-NH-$;
n is 1 or 2; and
Z is a hydrophobic anchor.

U.S. Pat. No. 4,925,852 discloses compounds which have the formulae:

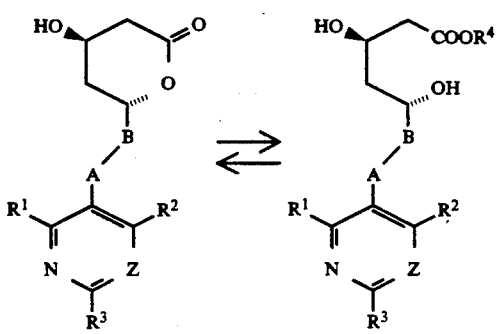

wherein
A-B denotes a radical of the formula $-CH=CH-$ or $-CH_2-CH_2-$;

Z denotes a radical of the formula $-CH$ or a nitrogen atom; and
$R^1$, $R^2$, $R^3$ and $R^4$ are selected from recited substituents.

SUMMARY OF THE INVENTION

The instant invention provides compounds having a phosphorus-containing group linked to a pyrimidinyl-containing group.

The compounds of the instant invention are inhibitors of the enzyme 3-hydroxy-3-methylglutarylcoenzyme A reductase (HMG-CoA reductase) and are thus inhibitors of cholesterol biosynthesis (hypocholesterolemic agents). The instant invention therefore provides a method for reducing or maintaining plasma cholesterol levels. The instant invention also provides methods for the treatment and/or prevention of atheroschlerosis, hyperlipodemia, and hyperlipoproteinaemia.

Further provided by the instant invention are pharmaceutical compositions containing the inventive compounds, as well as novel intermediates produced in the preparation of these compounds.

DETAILED DESCRIPTION OF THE INVENTION

The compounds provided by the instant invention have the following formula:

Compounds of the above formula are provided in which the group A is a moiety containing a phosphinyl group

which moiety is bonded to the moiety X through the phosphinyl group and which is capable of binding to the HMG binding domain of HMG-CoA reductase; Z is 5-pyrimidinyl, or a moiety containing a 5-pyrimidinyl group and bonded to the moiety X through the 5-pyrimidinyl group, which is capable of binding to a hydrophobic part of HMG-CoA reductase not utilized in binding HMG-CoA; and X is a moiety linking the groups A and Z; and salts, preferably pharmaceutically acceptable salts, thereof.

With respect to the the group A, the capability of binding to the HMG binding domain of HMG-CoA reductase may be indicated, for example, by the ability of the compound of the above formula to inhibit the activity of that enzyme. With respect to the group Z, the capability of binding to a hydrophobic part of HMG-CoA reductase not utilized in binding HMG-CoA may be indicated, for example, by an enhanced potency of the compound of the above formula in inhibiting the activity of HMG-CoA reductase relative to the activity exhibited by the corresponding compound in which Z is hydrogen.

Compounds of the above formula are also provided, which compounds are preferred, having the following formula (I):

$$R^4O-\underset{\underset{\underset{Z}{|}}{\overset{|}{X}}}{\overset{\overset{O}{\|}}{P}}-CH_2-\underset{\underset{OH}{|}}{\overset{\overset{R}{|}}{C}}-CH_2-\overset{\overset{O}{\|}}{C}-OR^5 \quad (I)$$

where

X is $-(CH_2)_a-$, $-CH=CH-$ (cis or trans), $-C\equiv C-$, or $-CH_2O-$ (preferably where $-CH_2-$ is linked to Z), and "a" is 1, 2 or 3;

R is hydrogen or lower alkyl;

Z is where
R$^1$, R$^2$ and R$^3$ are independently
(i) hydrogen,
(ii) alkyl,
(iii) aryl,
(iv) aralkyl,
(v) aralkoxy,
(vi) heterocyclo,
(vii) cycloalkyl,
(viii) alkoxy,
(ix) alkenyl,
(x) cycloalkenyl, or
(xi) halogen;
R$^4$ and R$^5$ are independently
(i) hydrogen,
(ii) alkyl,
(iii) aryl,
(iv) the group $$-\underset{\underset{R^6}{|}}{CH}-O-\overset{\overset{O}{\|}}{C}-R^7,$$

where R$^6$ is hydrogen, alkyl or aryl and R$^7$ is alkyl or aryl, or (v) if not already covered above, a group forming, together with the atoms to which it is bonded, an ester group which is hydrolyzable in vivo;

and salts, preferably pharmaceutically acceptable salts, thereof.

Thus, formula I encompasses preferred compounds of the following formulae IA through IH:

(IA) through (IH): structures with $R^4O-P(=O)(-CH_2-C(R)(OH)-CH_2-CO_2R^5)$ with varying Z-linker groups (C≡C, CH=CH cis, CH=CH trans, CH₂, CH₂CH₂, (CH₂)₃, CH₂-O, O-CH₂).

The term "alkyl" as employed herein alone or as part of another group includes both straight and branched chanin hydrocarbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkyl-aryl substituent, a haloaryl substituent, a cycloalkyl substituent, an alkyl-cycloalkyl substituent, a hydroxy substituent, an alkylamino substituent, an alkanoylamino substituent, an arylcarbonylamino substituent, a nitro substituent, a cyano substituent, a thiol substituent or an alkylthio substituent. The term "lower alkyl" as employed herein includes such alkyl groups as described above containing 1 to 6 carbon atoms in the normal chain.

The term "alkenyl" as employed herein alone or as part of another group refers to such groups as described above for alkyl, further containing at least one carbon to carbon double bond.

The term "cycloalkyl" as employed herein alone or as part of another group includes saturated cyclic hydrocarbon groups containing one or more rings and 3 to 12 ring carbons, preferably 3 to 8 ring carbons, which include cyclopropyl, cyclobutyl, cyclopentyl, cyclohexyl, cycloheptyl, cyclooctyl, cyclodecyl, cyclododecyl, and adamantyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "cycloalkenyl" as employed herein alone or as part of another group refers to such groups as described above for cycloalkyl, further containing at least one carbon to carbon double bond in the ring system.

The term "aryl" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1, 2 or 3 lower alkyl groups, halogens (e.g., Cl, Br or F), 1, 2 or 3 lower alkoxy groups, 1, 2 or 3 hydroxy groups, 1, 2 or 3 phenyl groups, 1, 2 or 3 alkanoyloxy group, 1, 2 or 3 benzoyloxy groups, 1, 2 or 3 haloalkyl groups, 1, 2 or 3 halophenyl groups, 1, 2 or 3 allyl groups, 1, 2 or 3 cycloalkylalkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, 1, 2 or 3 thiol groups, and/or 1, 2 or 3 alkylthio groups with the aryl group preferably containing 3 substituents.

The terms "aralkyl", "aryl-alkyl" or "aryl-lower alkyl" as used herein alone or as part of another group refer to alkyl or lower alkyl groups as discussed above having an aryl substituent, such as benzyl.

The terms "lower alkoxy", "alkoxy", or "aryloxy" or "aralkoxy" as employed herein alone or as part of another group include any of the above lower alkyl, alkyl, aryl or aralkyl groups linked to an oxygen atom.

The terms "lower alkylthio", "alkylthio", "arylthio", or "aralkylthio" as employed herein alone or as part of another group include any of the above lower alkyl, alkyl, aryl or aralkyl groups linked to a sulfur atom.

The terms "lower alkylamino", "alkylamino", "arylamino", or "arylalkylamino" as employed herein alone or as part of another group include any of the above lower alkyl, alkyl, aryl or arylalkyl groups linked to a nitrogen atom.

The term "alkanoyl" as used herein as part of another group refers to an alkyl group linked to a carbonyl group.

The term "halogen" or "halo" as used herein refers to chlorine, bromine, fluorine, iodine and CF₃, with chlorine or fluorine being preferred.

The term "heterocyclo" refers to fully saturated or unsaturated, monocyclic or bicyclic, aromatic or nonaromatic hydrocarbon groups having 5 or 6 atoms in each ring and at least one heteroatom in at least one ring. The heterocyclo group has 1 or 2 oxygen atoms, 1 or 2 sulfur atoms, and/or 1 to 4 nitrogen atoms in the ring. The heterocyclo group may be substituted with halogen (Cl, Br, F or CF₃), 1, 2 or 3 lower alkoxy groups, 1, 2, or 3 aralkyl groups, 1, 2 or 3 hydroxy groups, 1, 2 or 3 phenyl groups, 1, 2 or 3 alkanoyloxy groups, 1, 2 or 3 benzoyloxy groups, 1, 2 or 3 halophenyl groups, 1, 2 or 3 alkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, and 1, 2 or 3 thiol groups. Exemplary heterocyclo groups are 2- and 3-thienyl, 2- and 3-furyl, 2- and 3-pyrrolyl, 2-, 3- and 4-pyridyl, 2-, 4- and 5-imidazolyl, 2- and 3-pyrrolidinyl, 2-, 3- and 4-piperidinyl, 2-, 3- and 4-azepinyl, 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6-or 7-benzimidazolyl, 4-, 5-, 6- or 7-benzoxadiazolyl, and 4-, 5-, 6- or 7-benzofurazanyl.

The term "salt(s)" refers to basic salts formed with inorganic and organic bases. Exemplary basic salts include ammonium salts, alkali metal salts such as lithium, sodium and potassium salts (which are preferred), alkaline earth metal salts such as calcium and magnesium salts, salts with organic bases, for example, amine salts such as dicyclohexylamine salt, benzathine, N-methyl-D-glucamine, hydrabamine salts, salts with amino acids such as arginine and lysine and equivalent such salts. The nontoxic, pharmaceutically acceptable salts are preferred, although other salts are also useful, for example, in isolation or purification steps which may be employed during preparation.

In the compounds of formula I of the instant invention the preferred X "linking" groups are —CH₂—CH₂—, —CH=CH— (cis and trans), —C≡C—, and —CH₂O— where the latter group is bonded to Z through —CH₂—.

The group R is preferably hydrogen.

The groups R⁴ and R⁵ are preferably selected so that at least one of these groups, together with the atoms to which it is bonded, forms a free acid or salt group on the compound of formula I, preferably an alkali metal salt, or forms a group wherein the compound of formula I is an ester prodrug which is hydrolyzable in vivo. When R⁴ or R⁵ is the group

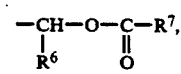

R⁶ is preferably hydrogen or lower alkyl and R⁷ is preferably lower alkyl.

It is preferred that the group R¹ contained in the group Z is aryl, particularly phenyl monosubstituted by a halogen atom, and that the group R² is alkyl, preferably lower alkyl such as isopropyl.

Particularly preferred compounds of the instant invention include:

(S)-4-[[[4-(4-fluorophenyl)-6-(1-methylethyl)-2-phenyl-5-pyrimidinyl]ethynyl]-methoxyphosphinyl]-3-hydroxybutanoic acid, methyl ester;

(S)-4-[[4-(4-fluorophenyl)-6-(1-methylethyl)-2-phenyl-5-pyrimidinyl]-ethynyl]-hydroxyphosphinyl]-3-hydroxybutanoic acid, disodium salt;

(S)-4-[[2-[4-(4-fluorophenyl)-6-(1-methylethyl)-2-phenyl-5-pyrimidinyl]ethenyl]-methoxyphosphinyl]-3-hydroxybutanoic acid, methyl ester;

(S)-4-[[2-[4-(4-fluorophenyl)-6-(1-methylethyl)-2-phenyl-5-pyrimidinyl]ethenyl]-hydroxyphosphinyl]-3-hydroxybutanoic acid, disodium salt;

(S)-4-[2-[4-(4-fluorophenyl)-6-(1-methylethyl)-2-phenyl-5-pyrimidinyl]ethyl]-methoxyphosphinyl-3-hydroxybutanoic acid, methyl ester; and (S)-4-[[2-[4-(4-fluorophenyl)-6-(1-methylethyl)-2-phenyl-5-pyrimidinyl]ethyl]-hydroxyphosphinyl]-3-hydroxybutanoic acid, disodium salt.

All stereoisomers of the compounds of the instant invention are contemplated, either in admixture or in substantially pure form. It is preferred to isolate compounds of the formula I or salts thereof in which the chiral center

of the phosphinyl side chain is in the S position.

The compounds of the instant invention may, for example, be in the free or hydrate form, and may be obtained by methods exemplified by the following Reaction Sequences.

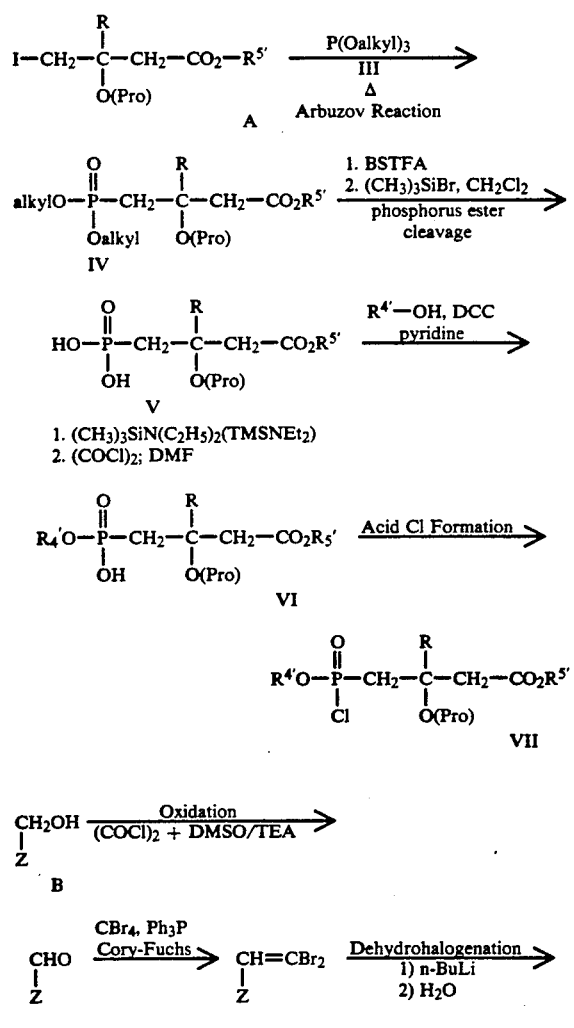

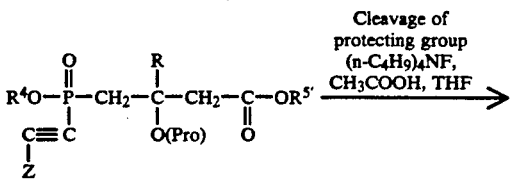

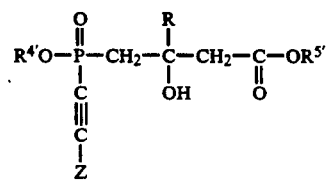

Compounds of the formula I where X is —C≡C— may be prepared by the method illustrated in the above Reaction Sequence A. As used herein, $R^{4'}$ and $R^{5'}$ denote aryl or alkyl, preferably alkyl groups. Protecting group "Pro" is a group which may be cleaved in subsequent steps without destruction of the remainder of the molecule, and is preferably -Si(t-butyl)(diphenyl).

The method illustrated begins by subjecting iodide A to an Arbuzov reaction by heating iodide A and phosphite III employing standard Arbuzov conditions and procedures to form the phosphonate IV.

Phosphonate IV is then subjected to phosphorus ester cleavage by treating a solution of phosphonate IV in an inert organic solvent, such as methylene chloride, sequentially with bis(trimethylsilyl)trifluoroacetamide (BSTFA) and trimethylsilyl bromide, under an inert atmosphere such as argon, to form the phosphonic acid V.

Phosphonic acid V is esterified by treating V in dry pyridine with, for example, a lower alkyl alcohol such as methanol and dicyclohexyl carbodiimide (DCC) and the resulting reaction mixture is stirred under an inert atmosphere, such as argon, to form phosphonic monoester VI.

Phosphonic monoester VI is then dissolved in an inert organic solvent, such as methylene chloride, benzene or tetrahydrofuran (THF) and treated with trimethylsilyldiethylamine (TMSNEt$_2$), and stirred under an inert atmosphere such as argon. The mixture is evaporated and then dissolved in methylene chloride or other appropriate inert organic solvent. The resulting solution is cooled to a temperature within the range of from about −10° C. to about 0° C., treated with oxalyl chloride and catalytic dimethylformamide and then evaporated to give crude phosphonochloridate VII. A novel fluoridate compound having the structure of VII, with the exception that —Cl is replaced by —F, may also be prepared by acid fluoride formation and employed wherever phosphonochloridate VII is employed as described following.

The phosphonochloridate VII is dissolved in inert organic solvent such as methylene chloride, benzene, pyridine or THF, the solution is cooled to a temperature within the range of from about −90° C. to about 0° C., and preferably from about −85° C. to about −30° C., and treated with a cooled (same range as solution of phosphonochloridate VII) solution of the lithium anion of acetylene X formed by treating X with a lithium source such as n-butyl lithium in THF or other inert solvent. Molar ratios of VII:X of within the range of from about 3:1 to about 1:1 and especially from about 1.5:1 to about 2:1 to form the acetylenic phosphinate XI are preferably employed.

The protecting group "Pro" of phosphinate XI may then be cleaved to form the acetylenic phosphinate IA$^1$. For example, when -O-(Pro) is a silyl ether, cleavage may be effected by treating XI in an inert organic solvent such as tetrahydrofuran, with glacial acetic acid and tetrabutylammonium fluoride to form the ester IA$^1$.

The iodide starting material A may be prepared starting with the following bromide C:

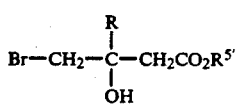     C where bromide C may itself be prepared by employing procedures analogous to those described in Acta. Chem. Scand., B. 1983, 37, 341–344.

Bromide C may be dissolved in solution in dimethylformamide (DMF) with imidazole and 4-dimethylamino pyridine, and the resulting solution treated with the halide of the protecting group "Pro", e.g. with t-butyldiphenyl silyl chloride, under an inert atmosphere such as argon to form the following protected ether D:

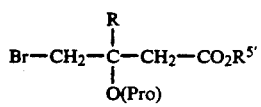     D

A solution of protected ether D in an inert organic solvent such as methyl ethyl ketone or DMF may be treated with sodium iodide under an inert atmosphere such as argon, to form iodide A.

The starting alcohol B may be obtained by methods analogous to those disclosed in U.S. Pat. No. 4,925,852, incorporated herein by reference. For example, a β-keto ester of the following formula E:

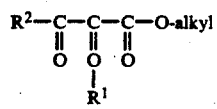     E may be reacted with a compound of the following formula F:

     F to yield the following dihydropyrimidine G or isomers thereof:

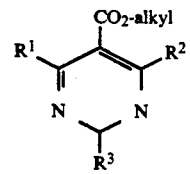     G

The condensation may be conducted in a solvent such as toluene, benzene, ethanol, dimethylsulfoxide, or dimethylformamide. A high boiling solvent, especially one forming an azeotrope with water, is preferred. The compound F may be employed free or in a salt, such as a hydrochloride, form. When compound F is employed in its salt form, an agent to liberate the compound to its free form is also preferably employed, such as potassium carbonate, sodium acetate or, especially, potassium acetate. The reaction is preferably conducted at a temperature of from about 25° C. to about 100° C., with higher temperatures being preferred. It is particularly preferred to conduct the reaction at the reflux temperature of the solvent. Molar ratios of E:F of from about 1:1 to about 1:5 are preferably employed.

The dihydropyrimidine G obtained may then be selectively oxidized with bromine, chloranil, elemental sulfur (S$_8$), palladium in decalin, or, preferably, 2,3-dichloro-5,6-dicyano-benzoquinone (DDQ). The reaction, preferably conducted at a temperature of from about 0° C. to about 80° C. in an inert solvent such as toluene, methylene chloride or ethanol yields the following pyrimidine H:

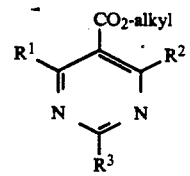     H

This reaction preferably employs an excess of oxidant, such as molar ratios of G:oxidizing agent of from about 1:1 to about 1:4.

The starting alcohol B may be obtained from pyrimidine H by a reduction reaction employing an agent such as lithium aluminum hydride (preferred molar ratios to pyrimidine H are from about 0.5:1 to about 2:1), lithium borohydride (preferred molar ratios to pyrimidine H are from about 0.5:1 to about 2:1), or, preferably, diisobutylaluminum hydride (DIBAL-H) (preferred molar ratios to pyrimidine H are from about 2:1 to about 6:1). An aprotic solvent such as tetrahydrofuran, methylene chloride or toluene is preferably employed. The reaction temperature is preferably from about −78° C. to about 25° C.

The acetylene X may be obtained beginning with the conversion of the starting alcohol B to aldehyde VIII by an oxidation reaction employing an oxidant such as pyridinium chlorochromate (PCC), tetra-n-propyl ammonium perruthenate (TPAP) and N-methyl morpholine oxide, or, especially, oxalyl chloride and dimethyl sulfoxide (DMSO)/triethylamine (TEA). The oxidant is preferably added in a solvent such as methylene chloride. Sufficient quantities of the oxidizing agent are employed to effect the reaction. A solvent such as tetrahydrofuran (THF) or, especially, methylene chloride (CH$_2$Cl$_2$), is preferably employed in conducting the reaction. When oxalyl chloride/DMSO is employed, it is also preferred to conduct the reaction at low temperatures such as −80° C. to −50° C.

Aldehyde VIII may be converted to the vinyl dibromide IX by a Cory-Fuchs reaction employing triphenyl phosphine (PPh₃) and carbon tetrabromide (CBr₄). This step is preferably conducted in a solvent such as acetonitrile, or especially, methylene chloride, at temperatures such as those from 0° C. to room temperature. PPh₃ is preferably employed in a molar ratio to compound VIII of about 3:1. The molar ratio of CBr₄ to compound VIII is preferably about 1.5:1. Carbon tetrachloride or CBrCl₃ may be employed in place of CBr₄, in which case the vinyl dichloride analog of compound IX is obtained. Either the vinyl dibromide or the vinyl dichloride may be employed in the subsequent step.

The vinyl compound IX then undergoes dehydrohalogenation with n-BuLi, quenched with water, to form the acetylene compound X. Alternatively, the vinyl compound IX may be converted to the lithium anion of acetylene X by contact with n-butyl lithium in a solvent such as tetrahydrofuran at low temperatures.

Alternatively, aldehyde VIII may be converted directly to acetylene X by treatment with dimethyl diazomethylphosphonate in the presence of potassium t-butoxide in an inert solvent such as tetrahydrofuran (−78° C. to 25° C.) under an inert atmosphere.

Esters of the formula IA¹ may be hydrolyzed to the corresponding basic salt or acid, that is, where R$_{xa}$ shown following is ammonium, alkali metal, alkaline earth metal, an amine and the like, by treatment with strong base such as lithium hydroxide or sodium hydroxide in the presence of dioxane, methanol, acetonitrile, tetrahydrofuran or other inert organic solvent under an inert atmosphere such as argon, preferably at a temperature of from about room temperature to 80° C., employing a molar ratio of base:ester IA¹ of within the range of from about 1:1 to about 1.1:1 to form the corresponding basic salt IA²:

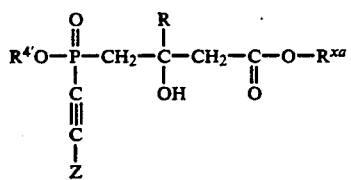

Compound IA² may then be treated with strong acid such as HCl to form the corresponding acid IA³:

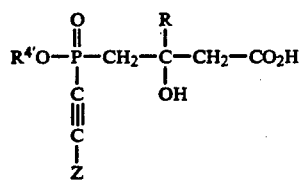

The ester IA¹ may be converted to the corresponding dibasic salt by treating ester IA¹ with strong base, for example, at 50°–60° C. employing a molar ratio of base:ester IA¹ of within the range of from about 2:1 to about 4:1 to form IA⁴:

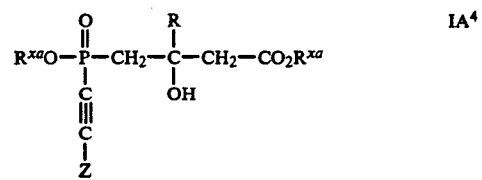

The dibasic salt IA⁴ may be converted to the corresponding acid by treatment with strong acid such as HCl to form the diacid.

Reaction Sequence B.
Preparation of compounds of the formula I where
X linkage is —CH=CH— (cis)

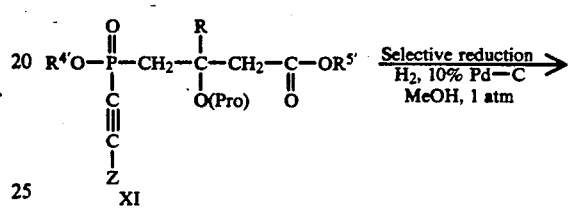

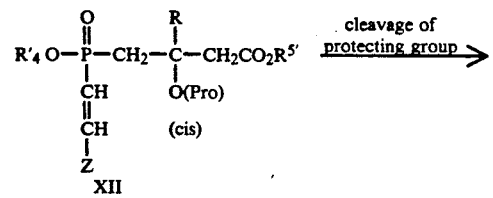

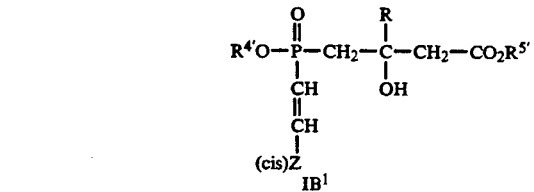

The above Reaction Sequence B illustrates preparation of compounds of the formula I where the X linkage is (cis) —CH=CH—. According to Reaction Sequence B, phosphinate compounds of the invention where X is (cis) —CH=CH— are formed by subjecting acetylenic phosphinate XI to selective reduction, for example, by treating XI with H₂ in the presence of a reduction catalyst such as palladium on carbon or palladium on barium carbonate in an inert organic solvent such as methanol to form the protected ether XII, where "Pro" is preferably -Si(t-butyl)diphenyl. Protected ether XII may then be subjected to ether cleavage and hydrolysis as described above to form the ester IB¹, the basic salt IB²:

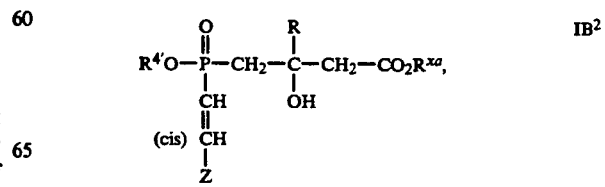

the acid IB³:

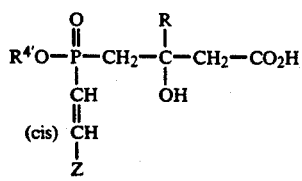

IB³ the dibasic salt IB⁴:

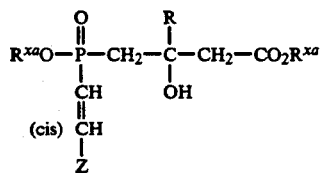

IB⁴ and the corresponding diacid.

Reaction Sequence C.
Preparation of compounds of
the formula I where X linkage is —CH=CH-(trans)

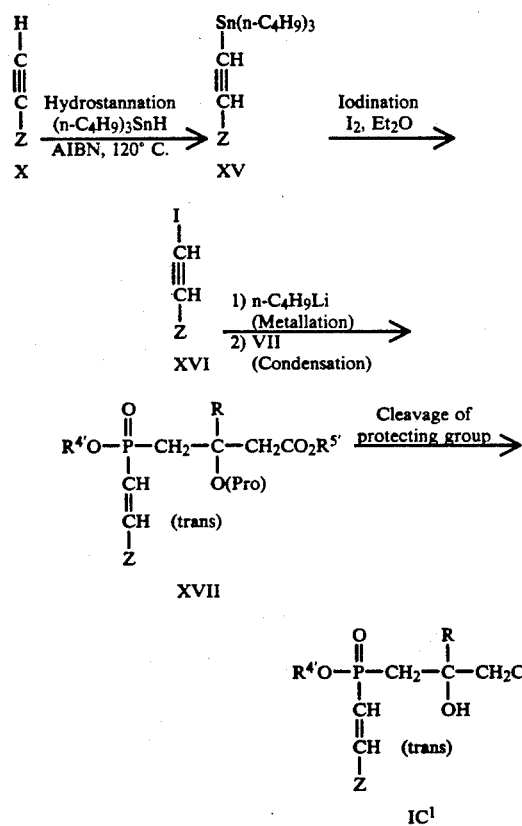

Reaction Sequence D.
Alternative preparation of compounds of
the formula I where X linkage is —CH=CH— (trans)

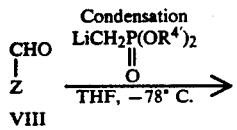

—continued
Reaction Sequence D.
Alternative preparation of compounds of
the formula I where X linkage is —CH=CH— (trans)

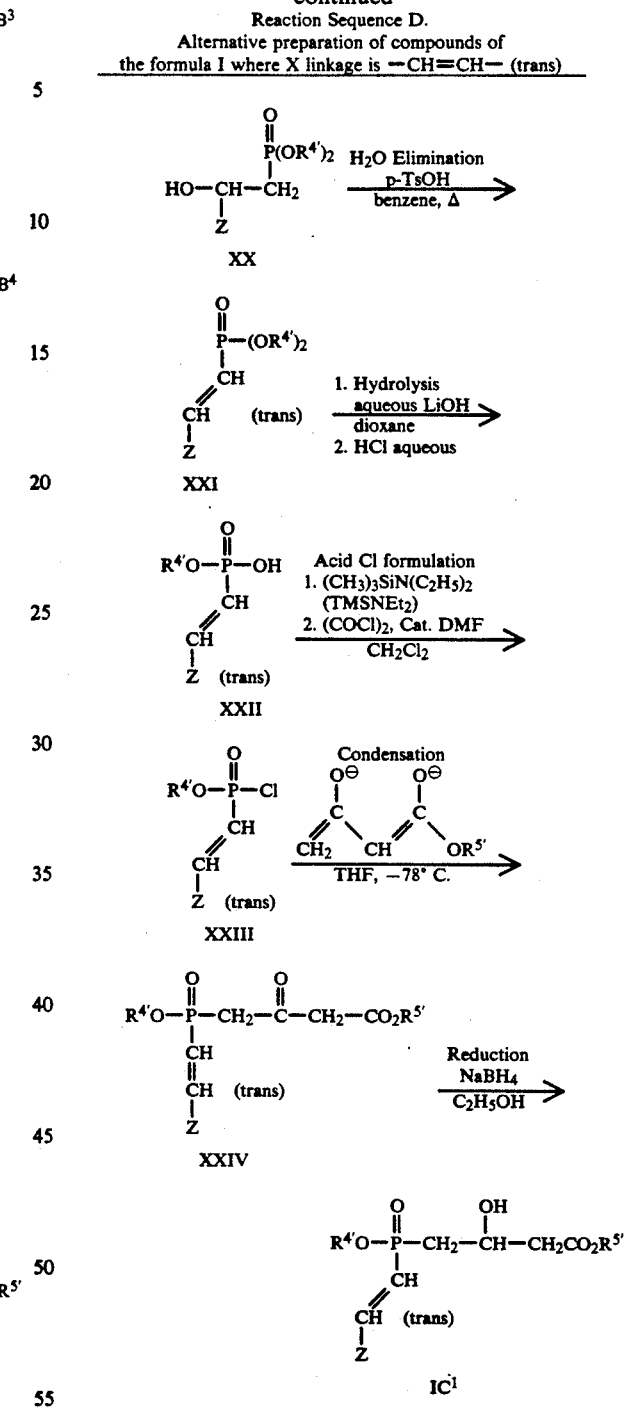

As can be seen from the above Reaction Sequence C, compounds of the formula I where the X linking group between the phosphorus atom and the anchor group Z is (trans) —CH=CH— may be prepared beginning by treating a mixture of acetylene compound X and (n-C₄H₉)₃SnH with a free radical initiator such as azobisisobutyrylnitrile (AIBN), hydrogen peroxide, benzoyl peroxide and the like in a catalytically effective amount, and heating the resulting solution to a temperature of within the range of from about 100° to about 160° C. under an inert atmosphere such as argon to form the vinyl stannane XV. A molar ratio of compound X:(n-C4H9)3-SnH of approximately 1:1.5 is preferably employed. A solvent is preferably not employed.

Vinyl stannane XV dissolved in an organic solvent such as ethyl ether, methylene chloride, tetrahydrofuran or chloroform may then be treated with iodine and stirred under an inert atmosphere such as argon to form vinyl iodide XVI. This reaction is preferably conducted at a temperature of from about room temperature to 50° C. Iodine is preferably employed in excess, preferably at a molar ratio of 3:1 or greater relative to vinyl stannane XV.

A cooled solution of vinyl iodide XVI ($-100°$ to 40° C., preferably $-100°$ to $-78°$ C.) in a dry organic solvent such as tetrahydrofuran or ethyl ether is treated with a metallating agent such as n-butyl or t-butyl lithium in an inert organic solvent such as hexane or tetrahydrofuran and the mixture is cooled at a temperature of from $-100°$ to $-40°$ C., preferably $-100°$ to $-78°$ C., under an inert atmosphere such as argon. The anion formed is added to a cooled ($-100°$ to $-40°$ C., preferably $-100°$ to $-78°$ C.) solution of phosphonochloridate VII (or novel phosphonofluoridate as discussed above with respect to Reaction Sequence A) at a molar ratio of XVI:VII of within the range of from about 1:1 to about 1:2 and preferably from about 1:1 to about 1:1.5 in a dry inert organic solvent such as tetrahydrofuran or ethyl ether to form XVII.

XVII is subjected to protecting group cleavage. For example, when "Pro" is -Si(t-butyl)-(diphenyl), silyl ether cleavage may be effected by treating a solution of XVII in an inert organic solvent such as tetrahydrofuran or acetonitrile with glacial acetic acid and a solution of (n-C4H9)4NF in an inert organic solvent such as tetrahydrofuran to form the hydroxy diester IC$^1$, which may then be hydrolyzed as described above to form the basic salt IC$^2$:

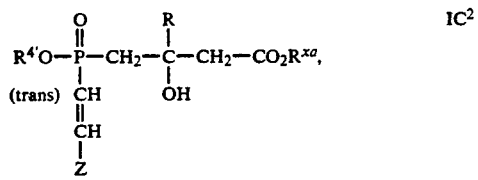

the acid IC$^3$:

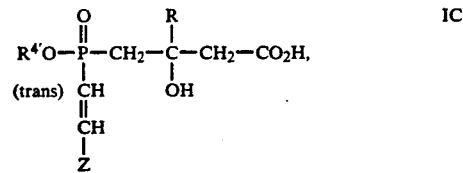

the dibasic salt IC$^4$:

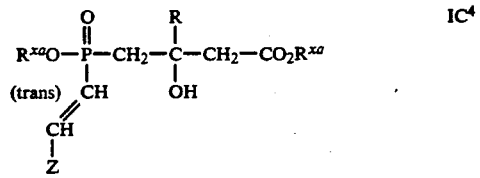

and the corresponding diacid.

In an alternative process, as shown in Reaction Sequence D, compounds of the formula I wherein the X linking group between the phosphorus atom and the anchor Z is (trans) —CH=CH— may be prepared by subjecting aldehyde VIII to a condensation reaction with a cooled ($-90$ to 0° C.) solution of, for example, dialkyl methylphosphonate and butyl lithium (LiCH2PO(R$^{4'}$)2) in the presence of an organic solvent such as tetrahydrofuran or ethyl ether to form the β-hydroxyphosphonate XX.

The β-hydroxyphosphonate XX may then be treated with p-toluenesulfonic acid in the presence of benzene or toluene while heating to a temperature within the range of from about 50 to about 120° C., preferably at reflux, to eliminate water and form the trans-olefin XXI, which is hydrolyzed by treating with aqueous alkali metal hydroxide, such as LiOH, in the presence of dioxane or other inert organic solvent and then with acid such as aqueous hydrochloric acid to form the monoacid ester XXII.

A solution of the monoacid ester XXII in dry methylene chloride may then be treated with trimethylsilyldiethylamine. The mixture is evaporated and the resulting oil is taken up in dry methylene chloride cooled to 0° C. and treated with oxalyl chloride and a catalytic amount of dimethyl formamide under an inert atmosphere such as argon to form phosphonochloridate XXIII. A fluoride compound having the structure of XXIII, with the exception that —Cl is replaced by —F, may also be prepared by acid fluoride formation and employed as follows.

Phosphonochloridate XXIII may be condensed with, for example, an alkyl acetoacetate dianion such as methyl acetoacetate dianion in the presence of an inert organic solvent such as tetrahydrofuran at reduced temperature of $-90$ to $-40°$ C. employing a molar ratio of phosphonochloridate:dianion within the range of from about 1:1 to about 0.75:1 to form the ketophosphonate XXIV, which is reduced by treatment with a reducing agent such as sodium borohydride in the presence of an alcohol solvent such as ethanol to form the phosphinate IC$^1$.

Diester IC$^1$ may then be hydrolyzed as described above to form the basic salt IC$^2$:

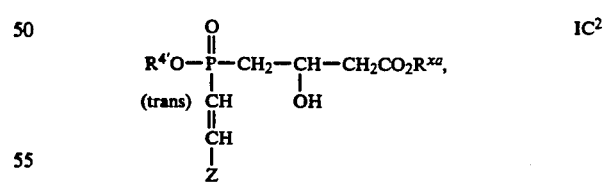

the acid IC$^3$:

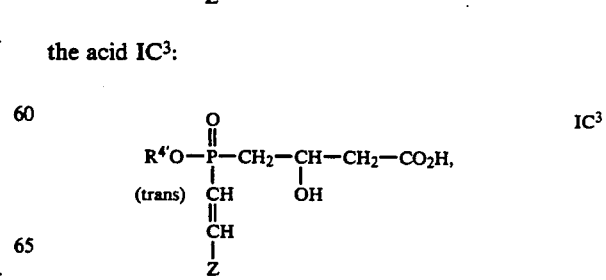

the dibasic salt IC$^4$:

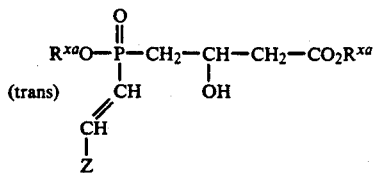

(trans) and the corresponding diacid.

Reaction Sequence E.
Preparation of compounds of the formula I where
X is —CH$_2$—, —CH$_2$CH$_2$— or —CH$_2$CH$_2$CH$_2$—

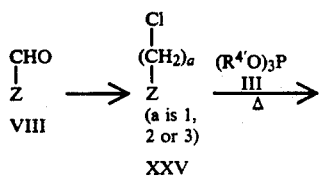

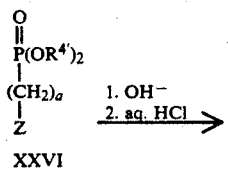

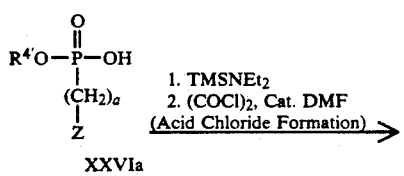

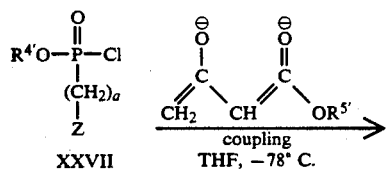

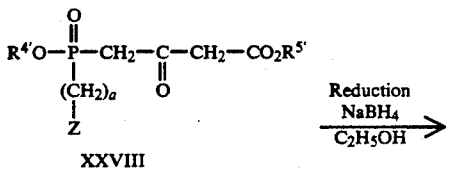

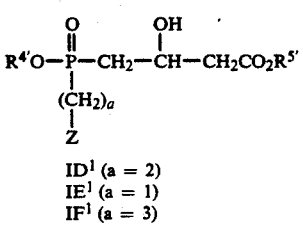

ID$^1$ (a = 2)
IE$^1$ (a = 1)
IF$^1$ (a = 3)

IC$^4$

Reaction Sequence F.
Alternative preparation of compounds of
the formula I where X is —CH$_2$—CH$_2$—

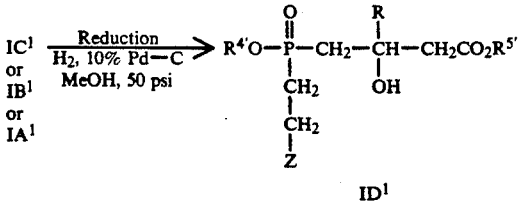

ID$^1$

According to Reaction Sequence E set forth above, compounds of the formula I where X is —(CH$_2$)$_a$— and a is 1, 2 or 3, that is —CH$_2$—, —CH$_2$CH$_2$— or —CH$_2$CH$_2$CH$_2$—, may be prepared starting with aldehyde VIII which is converted to halide XXV using conventional procedures. For example, the aldehyde VIII may be reduced with NaBH$_4$ in the presence of ethanol and ether to form the corresponding alcohol Z-CH$_2$OH (the starting material B of Reaction Sequence A) which is treated with mesyl chloride in the presence of an organic base such as triethylamine and a solvent such as methylene chloride to form the chloride XXV (a=1).

The chloride XXV is subjected to a condensation reaction where XXV is treated with phosphite III employing a molar ratio of III:XXV of within the range of from about 1:1 to about 10:1 and a temperature within the range of from about 100° to about 150° C. to form phosphonate diester XXVI. A solution of the phosphonate diester XXVI in a solvent such as dioxane is treated with a strong base such as an alkali metal hydroxide, for example, LiOH, and then an acid such as aqueous hydrochloric acid to form compound XXVIa. XXVIa is treated with TMSNEt$_2$, and then oxalyl chloride in the presence of an organic solvent such as dimethylformamide to form the corresponding phosphonochloridate XXVII. A fluoride compound having the structure of XXVII, with the exception that —Cl is replaced by —F, may also be prepared by acid fluoride formation and employed as follows. XXVII is condensed, for example, with an alkyl acetoacetate dianion such as methylacetoacetate dianion in the presence of an inert organic solvent such as tetrahydrofuran at reduced temperatures of from about −90° to about −40° C. employing a molar ratio of phosphonochloridate XXVII:dianion of within the range of from about 1:1 to 0.75:1 to form the ketophosphinate XXVIII. Ketophosphinate XXVIII may then be reduced to the corresponding phosphinate ID$^1$, IE$^1$ or IF$^1$ which may be hydrolyzed to form the corresponding (di)basic salts and (di)acids following procedures as described above.

As illustrated in the above Reaction Sequence F, phosphinate compounds of the invention where X is —CH$_2$—CH$_2$— may alternatively be formed by subjecting diester IC$^1$, IB$^1$ or IA$^1$ to catalytic reduction, for example by treating IC$^1$, IB$^1$ or IA$^1$ with H$_2$ in the presence of a reduction catalyst such as palladium on carbon and an inert organic solvent such as methanol at 50 psi to form the diester ID$^1$ which may be hydrolyzed as described above to form the basic salt ID$^2$:

the acid ID³:

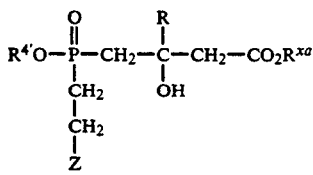

the dibasic salt ID⁴:

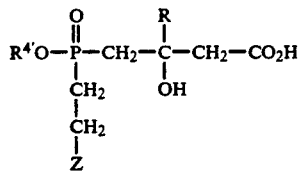

and the corresponding diacid.

Reaction Sequence G.
Preparation of compounds of the formula I where X is —CH₂O— bonded to Z through O

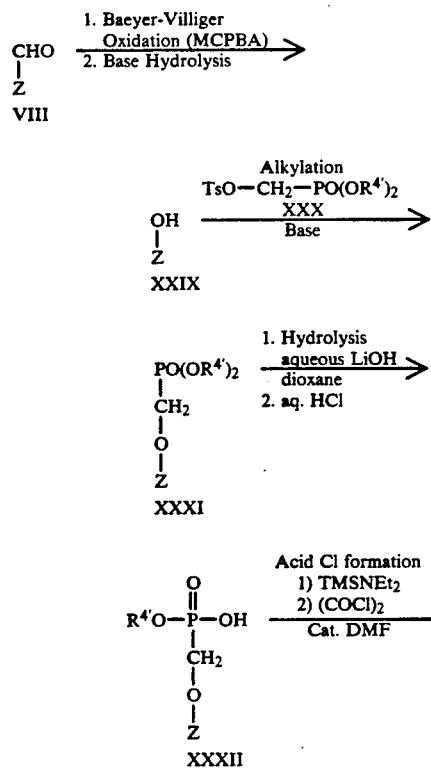

-continued
Reaction Sequence G.
Preparation of compounds of the formula I where X is —CH₂O— bonded to Z through O

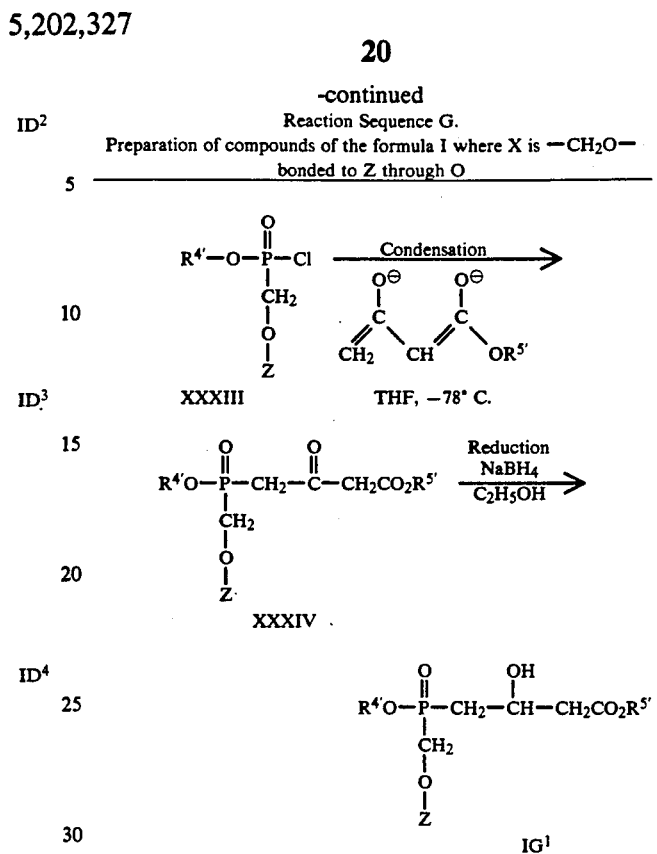

Referring to Reaction Sequence G above, compounds of the formula I where X is —Ch₂O— may be prepared. The starting aldehyde VIII is subjected to a Baeyer-Villiger oxidation by reacting VIII with meta-chloroperbenzoic acid (MCPBA) in the presence of an inert organic solvent such as methylene chloride, followed by a strong base such as an alkali metal hydroxide like KOH or NaOH and a solvent such as tetrahydrofuran to form the corresponding alcohol XXIX. The alcohol XXIX is alkylated by treating XXIX with sodium hydride in the presence of an inert organic solvent such as dimethylformamide under an inert atmosphere such as argon and a solution of, for example, a dialkyl tosyloxymethyl-phosphonate XXX, employing a molar ratio of XXX:XXIX of within the range of from about 1:1 to about 3:1 to form the corresponding dialkyl ester XXXI. The remainder of the synthesis described in Reaction Sequence G, that is, forming the monoester XXXII, chloride XXXIII (or fluoride), ketophosphinate XXXIV, diester IG¹ and the corresponding (di)-basic salts and (di)acids is similar to that set out hereinbefore with respect to Reaction Sequence E.

Reaction Sequence H
Preparation of Compounds of the formula I where X is —CH₂O— bonded to Z throught —CH₂—

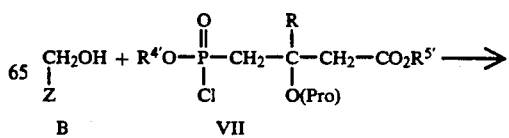

-continued
Reaction Sequence H
Preparation of Compounds of the formula I where X is —CH$_2$O— bonded to Z throught —CH$_2$—

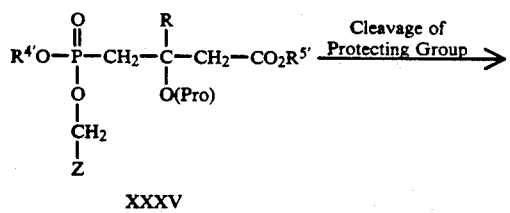
XXXV

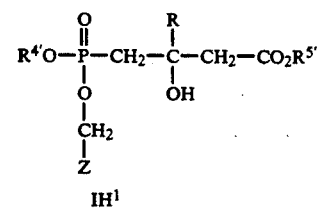
IH$^1$

Compounds of the formula I where X is —CH$_2$O— bonded to Z through the methylene group may be prepared by the method illustrated in the above Reaction Sequence H.

The method begins by coupling alcohol B, which may be prepared as discussed above with regard to Reaction Sequence A, with phosphonochloridate VII to form compound XXXV. The coupling reaction may be conducted in a solvent such as pyridine, alone or in admixture with tetrahydrofuran. A catalyst such as dimethylaminopyridine may be employed when desired.

Cleavage of the protecting group "Pro" to form the ester IH$^1$, as well as further treatment to form the corresponding (di)basic salts and (di)acids, may be conducted as discussed above in Reaction Sequence A.

The instant invention also provides novel intermediates which are described, and which may be prepared, as set forth in the above Reaction Schemes. These novel intermediates include those compounds designated above as the fluoride of VII, IX (and the correponding dichloride), X, XI, XII, XV, XVI, XVII, XX, XXI, XXII, XXIII (and fluoride), XXIV, XXV, XXVI, XXVIa, XXVII (and fluoride), XXVIII, XXIX, XXXI, XXXII, XXXIII (and fluoride), XXXIV and XXXV, including all stereoisomers thereof.

Thus, the instant invention provides novel intermediates of the following formulae IIa, IIb, IIc, IId, and IIe or salts thereof, $$\overset{L}{\underset{Z}{|}} \qquad \text{IIa}$$

where L is —CH=CBr$_2$, —CH=CCl$_2$, —C≡CH, —CH=CH—Sn(n—C$_4$H$_9$)$_3$, —CH=CH—I, —(CH$_2$)$_a$—Cl and "a" is 1, 2 or 3, or —OH; and Z is

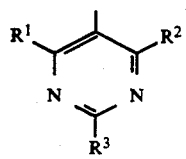

where,
R$^1$, R$^2$ and R$^3$ are independently
(i) hydrogen, (ii) alkyl, (iii) aryl, (iv) aralkyl, (v) aralkoxy, (vi) heterocyclo, (vii) cycloalkyl, (viii) alkoxy, (ix) alkenyl, (x) cycloalkenyl, or (xi) halogen;

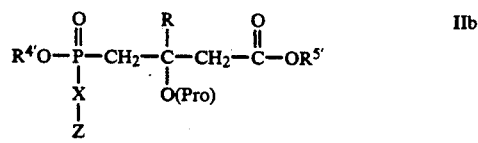

where X is —C≡C—, —CH=CH—, or —OCH$_2$— bonded to Z through —CH$_2$—;
"Pro" is a group which may be cleaved;
R$^4{'}$ and R$^{5'}$ are independently aryl or alkyl;
R is hydrogen or alkyl;
and Z is as defined above for formula IIa;

where Z is as defined above for formula IIa and (i) E$^1$ and E$^2$ are —OR$^{4'}$ where R$^{4'}$ is defined above for formula IIb and X* is —CH$_2$—CH(OH)—, —CH=CH—, —(CH$_2$)$_a$— and "a" is 1, 2 or 3, or —CH$_2$O—; (ii) E$^1$ is —OR$^{4'}$, E$^2$ is —Cl or —F and X* is —CH=CH—, —(CH$_2$)$_a$—, or —CH$_2$O—; or (iii) E$^1$ is —OR$^{4'}$, E$^2$ is —OH and X* is —CH=CH—, —(CH$_2$)$_a$— or —CH$_2$O— and "a" is 1,2 or 3;

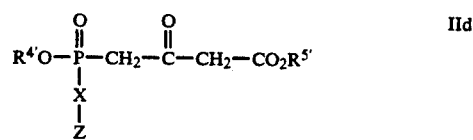

where X is —CH=CH—, —(CH$_2$)$_1$— and "a" is 1,2 or 3, or —CH$_2$O— where CH$_2$ or O is attached to Z and R$^{4'}$, Z and R$^{5'}$ are defined above for formula IIb;

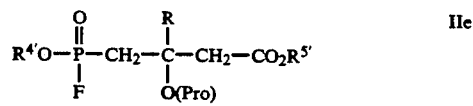

where R$^{4'}$, R$^{5'}$, R and "Pro" are as defined above for formula IIb.

The compounds of the invention may be prepared as racemic mixtures and may later be resolved to obtain the S-isomer which is preferred. However, the compounds of the invention may be prepared directly in the form of their S-isomers using the methods set forth in the above Reaction Sequences and in the working examples set out hereinafter. In this regard, British Patent No. 2,205,838 is incorporated herein by reference.

The compounds of the invention are inhibitors of 3-hydroxy-3-methyl-glutaryl coenzyme A (HMG—CoA) reductase and thus are useful in inhibiting cholesterol biosynthesis. The activity of the instant compounds therefor may be demonstrated by any of the tests set forth in British Patent No. 2,205,838 incorporated herein by reference. Generally, compound selectivity favoring greater inhibitory activity in hepatic tissue is an attribute for a cholesterol synthesis inhibitor.

The instant invention also provides a pharmaceutical composition comprising at least one of the inventive compounds, preferably a compound of formula I, or a pharmaceutically acceptable salt thereof in association with a pharmaceutically acceptable vehicle or diluent. The pharmaceutical composition may be formulated employing conventional solid or liquid vehicles or diluents, as well as pharmaceutical additives of a type appropriate to the mode of desired administration. The compounds may, for example, be administered by an oral route, such as in the form of tablets, capsules, granules or powders, or they may be administered by a parenteral route in the form of injectable preparations. Such dosage forms preferably contain from about 1 to 2000 mg of active compound per dosage. The dose to be administered depends on the unitary dose, the symptoms, and the age and the body weight of the patient, and may be determined by the skilled artisan. Exemplary pharmaceutical compositions of the instant invention are hypocholesterolemic, hypolipoproteinaemic, antiatheroschlerotic and/or hypolipidemic compositions comprising an amount of the inventive compound effective therefor.

The inventive compounds, preferably compounds of the formula I, or pharmaceutically acceptable salts thereof may be administered in a similar manner as known compounds suggested for use. in inhibiting cholesterol biosynthesis, such as lovastatin, particularly to subjects which are mammalian species such as humans, dogs, cats and the like. Thus, the compounds of the invention may be administered in an amount from about 1 to 2000 mg in a single dose or in the form of individual doses from 1 to 4 times per day, preferably 4 to 200 mg in divided dosages of 1 to 100 mg, suitably 0.5 to 50 mg 2 to 4 times daily or in sustained release form.

The instant invention also provides methods for the treatment or prevention of hypercholesterolemia, atheroschlerosis, hyperlipoproteinaemia and/or hyperlipidemia comprising the step of administering to a subject in need of said treatment(s) an inventive compound, preferably a compound of the formula I, or a pharmaceutically acceptable salt thereof in an amount effective therefor.

The following working Examples represent preferred embodiments of the present invention, and are not intended to limit the scope or spirit of the instant claims.

EXAMPLE 1

Preparation of (S)-4-[[[4-(4-Fluorophenyl)-6-(1-methylethyl)-2-phenyl-5-pyrimidinyl]ethynyl]-methoxyphosphinyl]-3-hydroxybutanoic acid, methyl ester (i)
4-(4-Fluorophenyl)-6-(1-methylethyl)-2-phenyl-5-ethoxycarbonyl-1,2-dihydropyrimidine

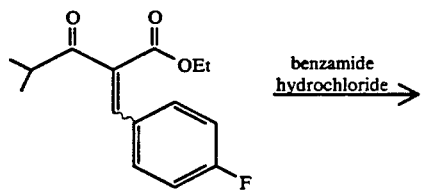 benzamide hydrochloride →

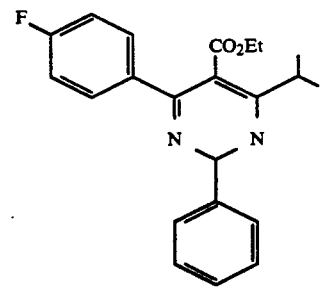

β-keto ester ethyl 3-oxo-2-(4-fluorobenzylidene)-4-methyl pentanoate (10.00 gm, 38 mmol) was added as a solution in toluene (5 ml) to a slurry of benzamide hydrochloride (8.13 gm, 52 mmol) and potassium acetate (KOAc) (5.59 gm, 57 mmol) stirring in toluene (200 ml) in a flask affixed with a Dean-Stark trap. The solution was refluxed for 20 hours, then cooled to room temperature and stirred for 24 hours. The solution was diluted with ether and filtered. The filtrate washed with saturated $NaHCO_3$, water, and brine, then dried over $Na_2SO_4$, filtered and concentrated to give a yellow oil. The oil was purified by flash chromatography on Merck silica gel in 30% ethyl acetate (EtOAc) in hexane. The fractions containing product were combined and concentrated to afford the title compound as a yellow foam (4.870 gm, 35%).

TLC: Rf=0.18 (20% EtOAc in hexane)

(ii)
4-(4-Fluorophenyl)-6-(1-methylethyl)-2-phenyl-5-ethoxycarbonyl-pyrimidine

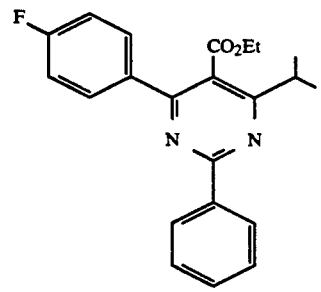

2,3-Dichloro-5,6-dicyanobenzoquinone (DDQ) (7.69 gm, 34 mmol) was added to a solution of 4-(4-fluorophenyl)-6-(1-methylethyl)-2-phenyl-5-ethoxycarbonyl-1,2-dihydropyrimidine obtained in step (i) above (10.200 gm, 28 mmol) in toluene (200 ml). The red solution was then heated at 50° C. for 3 hours. The solution was cooled to room temperature, then passed through a silica gel plug which was washed with 10% EtOAc in hexane. The filtrate was concentrated to give an amber oil. The oil was purified by flash chromatography on Merck silica gel in 15% EtOAc in hexane. Fractions containing the desired product were pooled and concentrated to give a clear oil which solidified to afford the title compound as a white, crystalline solid (8.800 gm, 87%) (mp 97°-99° C.).

TLC: Rf=0.75 (20% EtOAc in hexane)

Elemental Analysis: Calculated for $C_{22}H_{21}N_2FO_2$: analysis: C 72.51; H 5.81; N 7.69; F 5.21; found: C 72.45; H 5.79; N 7.72; F 5.12.

(iii)
4-(4-Fluorophenyl)-6-(1-methylethyl)-2-phenyl-5-hydroxymethylene-pyrimidine

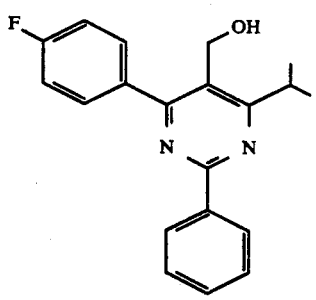

Diisobutylaluminum hydride (DIBAL-H) (1M in tetrahydrofuran (THF) (55 ml, 55 mmol) was added dropwise to a 0° C. solution of 4-(4-fluorophenyl)-6-(1-methylethyl)-2-phenyl-5-ethoxycarbonyl-pyrimidine obtained in step (ii) above (4.000 gm, 11 mmol) in THF (50 ml). The solution was then allowed to warm to room temperature and the mixture stirred for 3 hours. The solution was then cooled to 0° C. and quenched with saturated NH4Cl (55 ml). The solution was diluted with ether (100 ml) and the mixture was filtered through a celite pad and washed with ether. The filtrate was entirely organic and was dried over MgSO4, filtered and concentrated to give a yellow oil. The oil was dissolved in hot hexane and cooled to afford the title compound as a white solid (2.686 gm, 76%) (mp 183°-184° C.).

TLC: Rf=0.57 (50% EtOAc in hexane)

(iv)
4-(4-Fluorophenyl)-6-(1-methylethyl)-2-phenyl-5-formyl-pyrimidine

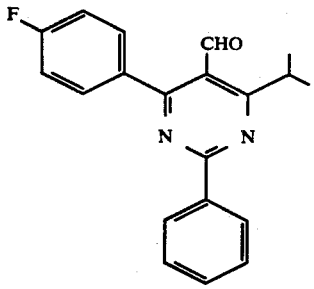

Dimethylsulfoxide (DMSO) (3.10 gm, 39.7 mmol) was added to a solution of oxalyl chloride (2.520 gm, 19.8 mmol) in methylene chloride (100 ml) which was cooled to −78° C. under argon. The solution was allowed to stir 15 minutes. Then, 4-(4-fluorophenyl)-6-(1-methylethyl)-2-phenyl-5-hydroxymethylene-pyrimidine obtained in step (iii) above (4.942 gm, 15.3 mmol) was added to the flask as a methylene chloride/THF (25 ml/10 ml) solution. The solution was stirred for 20 minutes and then triethylamine (10.6 ml) was added. The solution was stirred for an additional 10 minutes, then was warmed to room temperature. The solution was diluted with ether, washed with water and brine, then dried over Na2SO4, filtered and concentrated to afford a yellow solid. The solid was recrystallized from EtOAc/hexane to give the title compound as fine yellow needles (4.064 gm, 83%) (mp: 127-129° C.).

TLC: Rf=0.62 (30% EtOAc in hexane)

Elemental Analysis: for $C_{20}H_{17}N_2FO$: Analysis: C 74.98; H 5.35; N 8.75.; F 5.93; Found: C 74.83; H 5.50.; N 8.58; F 6.00.

(v)
4-(4-Fluorophenyl)-6-(1-methylethyl)-2-phenyl-5-(2,2-dibromovinyl)-pyrimidine

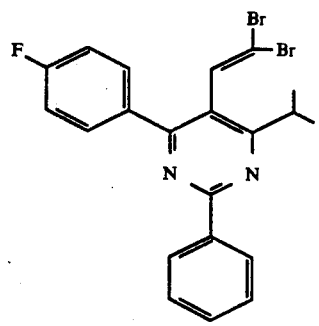

CBr4 (6.16 gm, 18.3 mmol) was added as a methylene chloride solution (20 ml) over 20 minutes to a mixture of triphenylphosphine (10.24 gm, 39 mmol) and the aldehyde 4-(4-fluorophenyl)-6-(1-methylethyl)-2-phenyl-5-formyl-pyrimidine obtained in step (iv) above (3.908 gm, 12.2 mmol) in methylene chloride (50 ml) which had been cooled to 0° C. The solution was stirred for 30 minutes and then warmed to room temperature over 15 minutes. The reaction was quenched with saturated NaHCO3 and the solution diluted with methylene chloride. The organic layer was washed with brine, then dried over Na2SO4, filtered and concentrated to about 35 ml. The solution was subjected to flash chromatography on Merck silica gel in 35-50% methylene chloride in hexane. The desired fractions were pooled and concentrated to give a yellow oil. The oil was dissolved in hot hexane and cooled to afford the title compound as large yellow crystals (7.338 gm, 83%) (mp 95°-98° C.).

TLC: Rf=0.75 (10% EtOAc in hexane)

Elemental Analysis: for $C_{21}H_{17}N_2Br_2F$: Analysis: C 52.97; H 3.60; N 5.88; Br 33.56; F 3.99; Found: C 53.41; H 3.75; N 5.71; Br 33.60;F 4.03.

(vi)
(S)-4-[[[4-(4-Fluorophenyl)-6-(1-methylethyl)-2-phenyl-5-pyrimidinyl]-ethynyl]-methoxyphosphinyl]-3-((t-butyl)diphenylsilyloxy)-butanoic acid, methyl ester

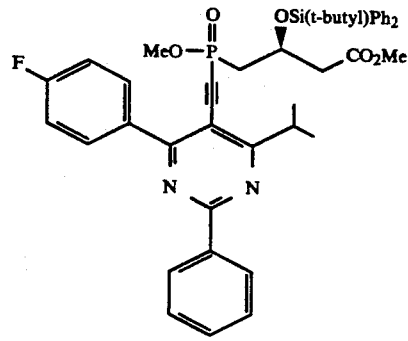

(a) Methyl 3S-hydroxyl-4-bromo butanoate

The title compound was prepared according to the methods described in Acta. Chem. Scand., B., 1983, 37, 341-344.

(b) Methyl 3S-((t-butyl)diphenylsilyloxy)-4-bromo butanoate

A solution of methyl 3S-hydroxyl-4-bromo butanoate obtained in step (a) above (4.0 g, 20.4 mmole), imidazole (6.94 g, 5.0 eq.), and 4-dimethylamino pyridine (4-DMAP) (12 mg, 0.005 eq.) in dry dimethylformamide (DMF) (40 ml) was treated with t-butyldiphenylsilyl chloride (5.84 ml, 1.1 eq.) and the homogeneous mixture stirred overnight under argon at room temperature. The mixture was partitioned between 5% $KHSO_4$ and EtOAc, the organic phase washed with $H_2O$ and brine then dried over anhydrous $Na_2SO_4$ and evaporated to give 9.32 g (100%) of the title compound as a clear, viscous oil with consistent $C^{13}$ NMR spectral data. TLC (3:1) Hex-EtOAc, product. Rf silyl ether=0.75, U. V. and PMA.

(c) Methyl 3S-((t-butyl)diphenylsilyloxy)-4-iodo butanoate

A solution of the crude methyl 3S-((t-butyl)-diphenylsilyloxy)-4-bromo butanoate obtained in step (b) above (9.32 g, 201 mmole) in methyl ethyl ketone (60 ml, over 4Å sieves) was treated with sodium iodide (15.06 g, 100.5 mmole, 5.0 eq.) and the yellow suspension refluxed for 5.0 hours under argon. The mixture was cooled, diluted with EtOAc, filtered, the filtrate washed with dilute $NaHSO_3$ (until colorless) and brine then dried over anhydrous $Na_2SO_4$ and evaporated in vacuo to give 10.17 g of a yellow oil. The crude oil was purified by flash chromatography on Merck silica gel (600 g, 50:1) eluting with (3:1) Hex-$CH_2Cl_2$ Product fractions were evaporated to give 7.691 g (74.2%, combined yield for both steps) of the title compound as a clear, colorless, viscous oil with consistent $C^{13}$ NMR spectral data and $H^1$ NMR spectral data. TLC (3:1) Hex-EtOAc, product. Rf=0.75, U.V. and PMA.

(d) Methyl 3S-((t-butyl)diphenylsilyloxy)-4-diisopropoxyphosphinyl butanoate

Methyl 3S-((t-butyl)diphenylsilyloxy)-4-iodo butanoate obtained in step (c) above (45.1 mmol, 21.70 g) was stirred under high vacuum for 30 minutes. Freshly distilled triisopropyl phosphite (0.451 mol, 93.92 g, 113.37 ml) was added in one portion and the reaction mixture was stirred under argon and heated in a 155° C. oil bath for 16.5 hours. The mixture was then cooled to room temperature. Excess triisopropyl phosphite and volatile reaction products were removed by short path distillation (10 mm Hg) followed by Kugelrohr distillation (0.50 mm Hg, 100° C., 8 hours). The product was further purified via flash chromatography (95 mm diam. column, 6" Merck silica gel, 6/3/1 hexane/acetone/toluene eluent, 2"/min flow rate, 50 ml fractions) to afford 17.68 g (33.96 mmol, 75% yield) of the title compound as a clear viscous oil. TLC: Silica gel Rf=0.32 (6:3:1 hexane/acetone/toluene).

$^1$H-NMR: (270MHz, $CDCl_3$); δ7.70°-7.65 (m, 4H); 7.45-7.35 (m, 6H); 4.57-4.44 (m, 3H); 3.59 (s, 3H); 2.94 and 2.88 (2xd, 1H, J=3.7 Hz); 2.65 and 2.60 (2xd, 1H, J=7.4 Hz); 2.24-1.87 (series of m, 2H); 1.19 and 1.12 (2xd, 12H, J=6.3 Hz); 1.01 (s, 9H).

(e) (S)-4-(Hydroxymethoxyphosphinyl)-3-[(t-butyl)-diphenylsilyl]oxy]butanoic acid, methyl ester, dicyclohexylamine (1:1) salt Methyl 3S-((t-butyl)diphenylsilyloxy)-4-diisopropoxyphosphinyl butanoate obtained in step (d) above (20.5 mmol, 10.66 g) was stirred under argon at room temperature, in 80 ml of dry $CH_2Cl_2$. This solution was treated dropwise (5 minutes) with bis(trimethylsilyl)trifluoroacetamide (BSTFA) (32.8 mmol, 8.44 g, 8.71 ml), followed by dropwise addition (10 minutes) of trimethylsilyl bromide (TMSBr) (51.3 mmol, 7.84 g, 6.75 ml). After stirring at room temperature for 20 hours, the reaction mixture was quenched with 200 ml of 5% aqueous $KHSO_4$ and stirred vigorously for 15 minutes. The aqueous layer was extracted 3X with EtOAc. The organic extracts were combined, washed 1X with brine, dried over $Na_2SO_4$ and concentrated in vacuo. The residue was azeotroped 2X with 50 ml of toluene. The precipitate which formed was suspended in toluene and filtered. The filtrate was concentrated and the azeotrope/filter process repeated. The resulting filtrate was evaporated in vacuo and then pumped under high vacuum for 5 hours. The resulting viscous clear oil was stirred under argon at room temperature in 50 ml of dry pyridine. This solution was treated in one portion with dicyclohexyl carbodiimide (DCC) (22.6 mmol, 4.65 g), followed by addition of methanol (41.0 mmol, 1.31 g, 1.67 ml). After stirring at room temperature for 20 hours, the reaction mixture was filtered through a Celite pad in a sintered glass funnel. The Celite was washed with EtOAc and the combined filtrates were evaporated in vacuo. The residue was redissolved in EtOAc and washed 2X with 5% aqueous $KHSO_4$ and 1X with brine. The organic extract was dried over $Na_2SO_4$, filtered, the filtrate concentrated, azeotroped 2X with toluene, suspended in toluene and filtered. The resulting filtrate was again concentrated, azeotroped, filtered and the filtrate evaporated in vacuo and placed under high vacuum for 6 hours to afford the phosphonate monoester as a clear, viscous oil (10.20 g, >100% yield, (TLC: silica gel Rf=0.50 (7:2:1 n-propanol (nPrOH)/$N$-$H_4OH$/$H_2O$) The phosphonate monoester [1:21 g was pumped under high vacuum for 4 hours, affording 1.16 g (2.57 mmol)] was dissolved in 10 ml of dry ethyl ether ($Et_2O$) and treated dropwise with dicyclohexylamine (2.65 mmol, 0.481 g, 0.528 ml). The resulting homogeneous solution sat at room temperature for 7 hours resulting in significant crystal formation. The mixture was stored at $-20°$ C. for 16 hours and then warmed to room temperature and filtered. The crystals were washed with cold, dry $Et_2O$ and then pumped under high vacuum over $P_2O_5$ for 18 hours. The crystals were subsequently pumped under high vacuum at 45° C. for 6 hours, affording 1.25 g (1.98 mmol, 77% yield) of the title compound as a white powdery solid. TLC: Silica gel Rf=0.57 (20% MeOH/$CH_2Cl_2$).

$^1$H-NMR (270 MHz, $CDCl_3$): δ7.71-7.65 (m, 4H); 7.40-7.32 (m, 6H); 4.02 (m, 1H); 3.52 (s, 3H); 3.28-3.22 (m, 1H); 3.11 (d, 3H, J=11 Hz); 2.77-2.64 (m, 2H); 2.62-2.56 (m, 1H); 1.92-1.08 (series of m, 22H); 1.00 (s, 9H).

Mas Spec (FAB) m/e 632 (M+H)+.

IR(KBr)3466-3457(broad), 3046, 3016, 2997, 2937, 2858, 2836, 2798, 2721, 2704, 2633, 2533, 2447, 1736, 1449, 1435, 1426, 1379, 1243, 1231, 1191. 1107, 1074, 1061, 1051, 820 $cm^{-1}$.

Elem. Anal. Calc'd for $C_{22}H_{31}O_6PSi$;.$C_{12}H_{23}N$: C, 64.63; H, 8.61; N, 2.22; Found: C, 64.51; H, 8.49; N, 2.18.

(f) (S)-4-(Methoxychlorophosphinyl)-3-[[(t-butyl)diphenylsilyl]oxy]-butanoic acid, methyl ester (S)-4-(Hydroxymethoxyphosphinyl)-3-[[(t-butyl)diphenylsilyl]oxy]butanoic acid, methyl ester, dicyclohexylamine (1:1) salt obtained in step (e) above (2.389 gm, 3.78 mmol) was partitioned between EtOAc and 5% KHSO₄. The EtOAc layer was washed 3X with 5% KHSO₄, then with brine, then dried (Na₂SO₄), filtered and stripped to give a colorless oil (phosphonic acid monomethyl ester). The oil was dissolved in dry CH₂Cl₂ (20 ml) and treated with N,N-diethyltrimethylsilylamine (1.154 gm, 7.94 mmol). After stirring at room temperature for one hour, the solvent was removed in vacuo and the residue was azeotroped with dry toluene (20 ml). The residue was re-dissolved in dry CH₂Cl₂ (20 ml), cooled to 0° C. and treated with dimethylformamide (DMF) (0.055 gm, 0.756 mmol) and oxalyl chloride (0.576 gm, 4.54 mmol). After 15 minutes, the solution was warmed to room temperature and stirred for an additional 45 minutes. The solvent was stripped and the yellow residue was azeotroped with toluene (20 ml) and dried in vacuo (oil pump) for 1 hour to yield the title compound.

(g) (S)-4-[[[4-(4-Fluorophenyl)-6-(1-methylethyl)-2-phenyl-5-pyrimidinyl]-ethynyl]-methoxyphosphinyl]-3-((t-butyl)diphenylsilyloxy)butanoic acid, methyl ester In a separate flask, a solution of 4-(4-fluorophenyl)-6-(1-methylethyl)-2-phenyl-5-(2,2-dibromovinyl)-pyrimidine obtained in step (v) above (1.000 gm, 2.10 mmol) in tetrahydrofuran (THF) (10 ml) was added dropwise to a −78° C. THF solution (15 ml) of n-butyl lithium (nBuLi) (2.5M in hexane, 1.68 ml, 4.20 mmol). The solution was allowed to stir 1 hour at −78° C., then cannulated into a THF solution (20 ml) of (S)-4-(methoxychlorophosphinyl)-3-[[(t-butyl)diphenylsilyl]oxy]butanoic acid, methyl ester obtained in step (f) above which had also been cooled to −78° C. The resultant solution was stirred for 30 minutes, then quenched with saturated NH₄Cl (15 ml) and warmed to 0° C. Then, saturated NaHCO₃ was added to the solution which was subsequently warmed to room temperature. The mixture was diluted with ether and the organic layer was washed with brine, then dried over Na₂SO₄, filtered and concentrated to give an orange oil. The oil was purified by flash chromatography on Merck silica gel in 30-50% EtOAc in hexane. The desired fractions were combined and evaporated to afford the title compound as yellow foam (0.732 gm, 49%). TLC: $R_f$=0.50 (50% EtOAc in hexane).

(vii)
(S)-4-[[[4-(4-Fluorophenyl)-6-(1-methylethyl)-2-phenyl-5-pyrimidinyl]-ethynyl]-methoxyphosphinyl]-3-hydroxybutanoic acid, methyl ester

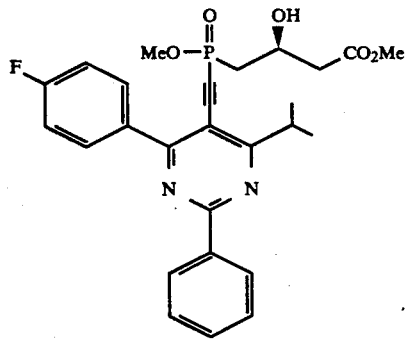

Tetrabutylammonium fluoride ((Bu)₄NF) (1.0M in THF, 2.91 ml, 2.91 mmol) was added to a mixture of (S)-4-[[[4-(4-fluorophenyl)-6-(1-methylethyl)-2-phenyl-5-pyrimidinyl]-ethynyl]-methoxyphosphinyl]-3-((t-butyl)diphenylsilyloxy)-butanoic acid, methyl ester obtained in step (vi) above (0.709 gm, 0.97 mmol) and acetic acid (0.233 gm, 3.89 mmol) in THF (10 ml). The solution was allowed to stir for 20 hours at room temperature. The solution was diluted with ether and then washed with 5% KHSO₄ (3x). The aqueous layers were back-extracted with EtOAc (3x). The organic layers were pooled and washed with brine, then dried over Na₂SO₄, filtered and concentrated to afford a yellow gum. The gum was redissolved in EtOAc, then washed with saturated NaHCO₃, 5% KHSO₄ and brine, then dried over Na₂SO₄ filtered and concentrated to a yellow oil. The oil was dissolved in methanol (15 ml) at 0° C. and treated with CH₂N₂. Excess CH₂N₂ was removed in a stream of argon, and the solution was concentrated to a yellow oil. The oil was purified by flash chromatography on Merck silica gel in 40% acetone in hexane. The desired fractions were pooled and concentrated to afford the title compound as a clear oil (0.315 gm, 64%). TLC: $R_f$=0.49 (50% acetone in hexane).

EXAMPLE 2

Preparation of (S)-4-[[[4-(4-Fluorophenyl)-6-(1-methylethyl)-2-phenyl-5-pyrimidinyl]-ethynyl]-hydroxyphosphinyl]-3-hydroxybutanoic acid, disodium salt

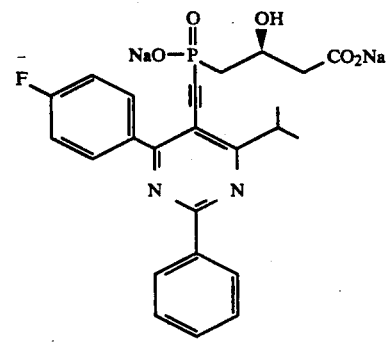

NaOH (1M in water, 1.82 ml, 1.82 mmol) was added to a solution of (S)-4-[[[4-(4-fluorophenyl)-6-(1-methylethyl)-2-phenyl-5-pyrimidinyl]-ethynyl]methoxyphosphinyl]-3-hydroxybutanoic acid, methyl ester obtained in Example 1 above (0.310 gm, 0.61 mmol) in dioxane (10 ml). The solution was allowed to stir for 5 hours at room temperature and then concentrated to give a white solid. The residue was dissolved in water and chromatographed on HP-20 resin, eluting first with water (150 ml), then with 50% methanol (MeOH) in water (300 ml), then with MeOH (150 ml). The desired fractions were pooled and concentrated. The residue was taken up in water and lyophilized to give the title compound as a fluffy white solid (0.250 gm, 78%) (mp: 310° C. (decomp)). The title compound was hydrated with 1.10 moles of water. TLC: $R_f$=0.68(6:3:1, n-propanol:NH₄OH:H₂O)

Elemental Analysis: for $C_{25}H_{22}N_2FNaPO_5 \cdot 1.10$ moles: H₂O Analysis: C 54.98; H 4.46; N 5.13; F 3.48; P 5.67; Found: C 54.75; H 4.63; N 5.36; F 3.59; P 5.66.

Optical Rotation: $[\alpha]_D$=1.4°(MeOH, C=3.5 mg/ml)

EXAMPLE 3

Preparation of
(S)-4-[[2-[4-(4-Fluorophenyl)-1-methylethyl)-2-phenyl-5-pyrimidinyl]ethenyl]-methoxyphosphinyl]-3-hydroxybutanoic acid, methyl ester (i)
4-(4-Fluorophenyl)-6-(1-methylethyl)-2-phenyl-5-ethinyl-pyrimidine

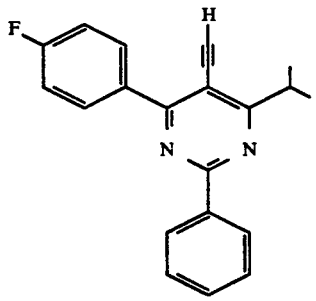

4-(4-Fluorophenyl)-6-(1-methylethyl)-2-phenyl-5-(2,2-dibromovinyl)-pyrimidine obtained as in step (v) of Example 1 above (3.476 gm, 7.30 mmol) was added as a THF solution (10 ml) to a −78° C. solution of nBuli (2.5M in hexane, 6.13 ml, 15.22 mmol) in THF (30 ml). The solution was allowed to stir one hour at −78° C., then was quenched with saturated NH₄Cl. The solution was warmed to 0° C. and saturated NaHCO₃ was added. After warming to room temperature, the mixture was diluted with EtOAc and the organic layer was washed with brine, then dried over Na₂SO₄, filtered and concentrated to give a clear oil. The oil was dissolved in hot hexane and cooled to afford the title compound as white needles (2.004 gm, 87%) (mp 57°-159° C.).

TLC: $R_f$=0.50 (2% EtOAc in hexane)

Elemental Analysis: calculated for $C_{21}H_{17}N_2F$: Analysis: C 79.72; H 5.42; N 8.86; F 5.96; Found: C 79.28; H 5.51; N 8.69; F 5.85.

(ii)
4-(4-Fluorophenyl)-6-(1-methylethyl)-2-phenyl-5-(2-tri-n-butyltin vinyl)-pyrimidine

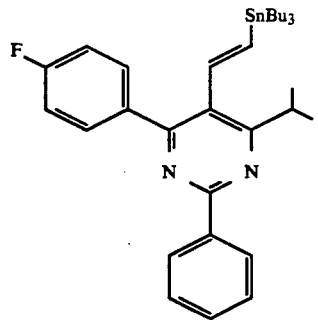

A mixture of tri-n-butyltin hydride (3.11 gm, 10.7 mmol), 4-(4-fluorophenyl)-6-(1-methylethyl)-2-phenyl-5-ethinyl-pyrimidine obtained in step (i) above (1.880 gm, 5.95 % mmol) and azobisisobutyrylnitrile (AIBN) (0.062 gm, 0.38 mmol) was heated to 140° C. for five hours. The solution was then cooled to room temperature and diluted with ether (to 50 ml). The solution obtained contained the title compound.

(iii)
4-(4-Fluorophenyl)-6-(1-methylethyl)-2-phenyl-5-(2-iodovinyl)-pyrimidine

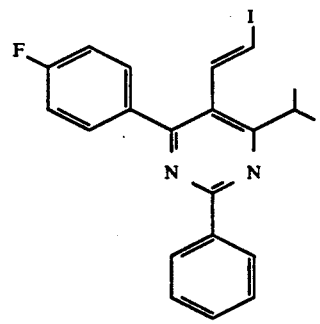

2,6-Lutidine (1.913 gm, 17.8 mmol) and then iodine (4.25 gm, 16.73 mmol) were added to the solution obtained in step (ii) above which was stirred for 15 hours at room temperature. The solution was then quenched with 10% Na₂S₂O₃ in saturated NaHCO₃. The mixture was diluted with ether, washed with 10% Na₂S₂O₃ in saturated NaHCO₃(2x) and brine, then dried over Na₂SO₄, filtered and concentrated to give a yellow oil. The oil was purified by flash chromatography on Merck silica gel in 10-20% toluene in hexane. The desired fractions were combined and concentrated to afford the title compound as a yellow solid (1.064 gm, 40%) (mp=119°-122° C.).

TLC: $R_f$=0.44 (1% EtOAc in hexane)

Elemental Analysis: Calculated for $C_{21}H_{18}N_2FI$: Analysis: C 56.77; H 4.08; N 6.31; F 4.28; I 28.56; Found: C 57.17; H 4.03; N 6.22; F 4.53; I 28.79.

(iv)
(S)-4-[[[4-(4-Fluorophenyl)-6-(1-methylethyl)-2-phenyl-5-pyrimidinylethenyl]methoxyphosphinyl]-3-((t-butyl)-diphenylsilyl(oxy)-butanoic acid, methyl ester

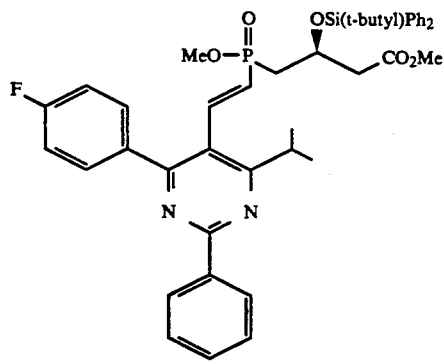

(S)-4-(Hydroxymethoxyphosphinyl)-3-[[(t-butyl)-diphenylsilyl]oxy]butanoic acid, methyl ester, dicyclohexylamine (1:1) salt obtained in step (vi)(e) of Example 1 above (2.690 gm, 4.25 mmol) was partitioned between EtOAc and 5% KHSO₄. The EtOAc layer was washed 3X with 5% KHSO₄, then with brine, then dried (Na₂SO₄), filtered and stripped to give a colorless oil (phosphonic acid monomethyl ester). The oil was dissolved in dry CH₂Cl₂ (20 ml) and treated with N,N-diethyltrimethylsilylamine (1.235 gm, 8.50 mmol). After stirring at room temperature for one hour, the solvent was removed in vacuo and the residue was azeotroped with dry toluene (20 ml). The residue was re-dissolved in dry CH$_2$Cl$_2$ (20 ml), cooled to 0° C. and treated with DMF (0.062 gm, 0.85 mmol) and oxalyl chloride (0.647 gm, 5.1 mmol). After 15 minutes, the solution was warmed to room temperature and stirred for an additional 45 minutes. The solvent was stripped and the phosphonochloridate (S)-4-(chloro-methoxyphosphinyl)-3-[[(t-butyl)diphenylsilyl]-oxy]-butanoic acid, methyl ester, obtained as a yellow residue, was azeotroped with toluene (20 ml) and dried in vacuo (oil pump) for 1 hour.

In a separate flask, a solution of 4-(4-fluorophenyl)-6-(1-methylethyl)-2-phenyl-5-(2-iodovinyl)-pyrimidine obtained in step (iii) above (1.050 gm, 2.36 mmol) in THF (5 ml) was added dropwise to a solution of t-butyl lithium (tBuLi) (1.7M pentane, 2.78 ml, 4.72 mmol) in THF (10 ml) cooled to −100° C. stirring under argon. The solution was allowed to stir 20 minutes at −100° C. and cannulated over 10 minutes into a THF solution (15 ml) of the above-prepared phosphonochloride which had also been cooled to −100° C. The solution was stirred 15 minutes at −100° C., then quenched with saturated NH$_4$Cl, warmed to 0° C. and then saturated NaHCO$_3$ was added to the solution. The solution was diluted with ether and the organic layer was washed with brine, then dried over Na$_2$SO$_4$, filtered and concentrated to give a pale yellow oil. The oil was purified by flash chromatography on Merck silica gel in 40–60% EtOAc in hexane. The desired fractions were combined and evaporated to afford the title compound as a yellow foam (0.488 gm, 27%). TLC: R$_f$=0.30 (50% EtOAc in hexane).

(v)
(S)-4-[2'-4-(4-Fluorophenyl)-6-(1-methylethyl)-2-phenyl-5-pyrimidinyl]ethenyl]methoxyphosphinyl]-3-hydroxybutanoic acid, methyl ester)

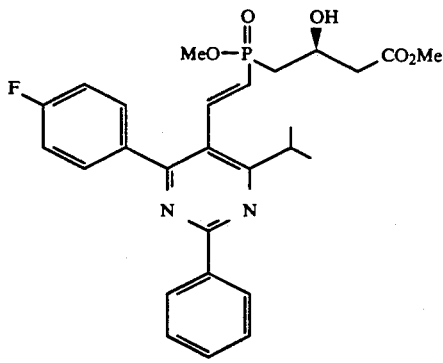

(C$_4$H$_9$)$_4$NF (1M in THF, 1.90 ml, 1.90 mmol) was added to a solution of (S)-4-[[[4-(4-fluorophenyl)-6-(1-methylethyl)-2-phenyl-5-pyrimidinyl]ethenyl]-methoxyphosphinyl]-3-[[(t-butyl)diphenylsilyl]oxy]-butanoic acid, methyl ester obtained in step (iv) above (0.475 gm, 0.63 mmol) and acetic acid (0.151 gm, 2.52 mmol) in THF (10 ml) and was stirred for 16 hours at room temperature. The solution was diluted with EtOAc and washed with 5% KHSO$_4$ (3x). The aqueous layers were back-extracted with EtOAC (2x). The organic layers were combined and washed with brine, then dried over Na$_2$SO$_4$, filtered and concentrated to give a yellow oil. The oil was dissolved in ether and treated with CH$_2$N$_2$. Excess CH$_2$N$_2$ was removed in a stream of argon and the solution was concentrated to give an orange oil. The oil was purified by flash chromatography on Merck silica gel in 50% acetone in hexane. The desired fractions were pooled and concentrated to afford the title compound as a clear oil (0.300 gm, 93%). TLC: R$_f$=0.47 (50% acetone in hexane).

EXAMPLE 4

Preparation of
(S)-4-[2-[4-(4-Fluorophenyl)-6-(1-methylethyl)-2-phenyl-5-pyrimidinyl]-ethenyl]hydroxyphosphinyl]-3-hydroxybutanoic acid, disodium salt

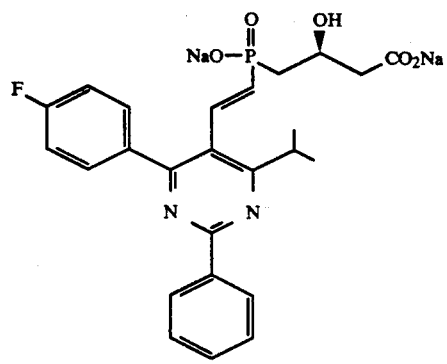

A solution of NaOH (1M in H$_2$O, 1.01 ml, 1.01 mmol) was added dropwise to a solution of (S)-4-[[2-[4-(4-fluorophenyl)-6-(1-methylethyl)-2-phenyl-5-pyrimidinyl]ethenyl]methoxyphosphinyl]-3-hydroxybutanoic acid, methyl ester obtained in Example 3 above (0.172 gm, 0.34 mmol) in dioxane (10 ml). The solution was warmed to 55° C. and stirred for 3 hours. The mixture was then concentrated to a white solid. The solid was dissolved in water and chromatographed on HP-20 resin, eluting first with water (150 ml), then with 50% MeOH in water (300 ml), and finally MeOH (50 ml). The desired fractions were pooled and concentrated. The resultant white solid was dissolved in water and lyophilized to give the title compound as a fluffy white solid (0.140 gm, 79%) (mp: 395° C. (decomp)). The title compound was hydrated with 2.41 moles of water.

TLC R$_f$=0.65 (6:3:1, n-propanol:NH$_4$OH:H$_2$O).

Elemental Analysis: Calculated for C$_{25}$H$_{24}$N$_2$FNa$_2$PO$_5$*2.41 H$_2$O: analysis: C 52.51; H 5.08; N 4.90; F 3.323; P 5.42; found: C 52.63; H 4.84; N 4.77; F 3.64; P 5.66.

Optical Rotation: [α]$_D$= −1.5° C. (MeOH, c=0.33)

EXAMPLE 5

Preparation of (S)-4-[[2-[4-(4-Fluorophenyl)-(1-methylethyl)-2-phenyl-5-pyrimidinyl]ethyl]-methoxyphosphinyl]-3-hydroxybutanoic acid, methyl ester

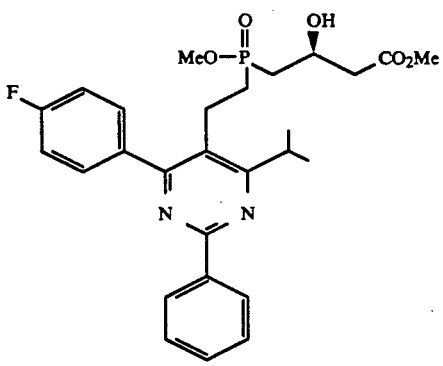

10% Pd/C (0.026 gm, 0.024 mmol) was added to a methanol solution (30 ml) of (S)-4-[[2-[4-(4-fluorophenyl)-6-(1-methylethyl)-2-phenyl-5-pyrimidinyl]ethenyl]methoxyphosphinyl]-3-hydroxybutanoic acid, methyl ester obtained in Example 3 above (0.125 gm, 0.24 mmol) which had been purged with argon for 15 minutes. The solution was then placed under 50 psi of hydrogen on a Parr apparatus and shaken for 6 days. The flask was then taken off the Parr apparatus and the solution filtered through a pad of celite which was washed with methanol. The filtrate was concentrated to give a clear oil which was subsequently purified by flash chromatography on Merck silica gel in 30–70% acetone in hexane. Product fractions were combined and concentrated to afford the title compound as a white solid (0.080 gm, 64%). TLC: $R_f$=0.41 (50% acetone in hexane).

EXAMPLE 6

Preparation of (S)-4-[[2-[4%(4-Fluorophenyl)-6-(1-methylethyl)-2-phenyl-5-pyrimidinyl]ethyl]-hydroxyphosphinyl]-3-hydroxybutanoic acid, disodium salt

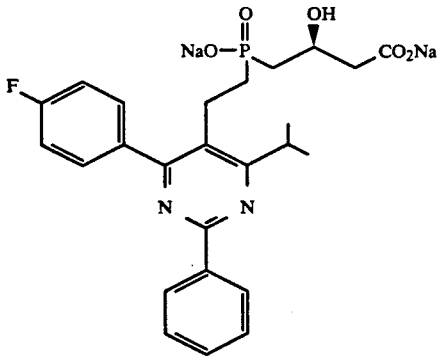

NaOH (1M in H$_2$O, 0.468 ml, 0.468 mmol) was added dropwise to (S)-4-[[2-[4-(4-fluorophenyl)-6-(1-methylethyl)-2-phenyl-5-pyrimidinyl]ethyl]-methoxyphosphinyl]-3-hydroxybutanoic acid, methyl ester obtained in Example 5 above (0.080 gm, 0.156 mmol) in dioxane (5 ml) and warmed to 60° C. and stirred for 3.5 hours. The mixture was then concentrated to a white solid.

The solid was dissolved in water and chromatographed on HP-20 resin, eluting first with water (125 ml) and then with 50% MeOH in water (300 ml). The desired fractions were pooled and concentrated. The resultant white solid was dissolved in water and lyophilized to give the title compound as a fluffy white solid (0.070 gm, 85%) (mp 310° C. (decomp)). TLC: $R_f$=0.69 (6:3:1, n-propanol:NH$_4$OH:H$_2$O).

Elemental Analysis: Calculated for C$_{25}$H$_{26}$N$_2$FNa$_2$PO$_5$*2.73 H$_2$O: analysis: C 51.80 ; H 5.47 ; N 4.83 ; F 3.28; P 5.34; found: C 51.86; H 5.48 ; N 4.76; F 3.50; P 5.40.

Optical Rotation: $[\alpha]_D$=−1.3° C. (MeOH, c=3.1 mg/ml)

What is claimed is:

1. A compound having the following formula (I):

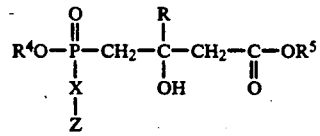

where
X is —(CH$_2$)$_a$—, —CH=CH—, —C≡C—, or —CH$_2$O— (where either —CH$_2$— or —O — is attached to Z) and "a" is 1, 2, or 3;
R is hydrogen or lower alkyl;
Z is

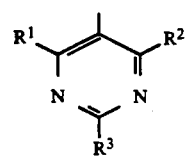

where R$^1$, R$^2$ and R$^3$ are independently
(i) hydrogen,
(ii) alkyl,
(iii) aryl,
(iv) aralkyl,
(v) aralkoxy,
(vi) heterocyclo,
(vii) cycloalkyl,
(viii) alkoxy,
(ix) alkenyl,
(x) cycloalkenyl, or
(xi) halogen; and
R$^4$ and R$^5$ are independently
(i) hydrogen,
(ii) alkyl,
(iii) aryl,
(iv) the group

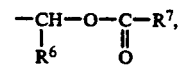

where R$^6$ is hydrogen, alkyl or aryl and R$^7$ is alkyl or aryl, or
(v) if not already covered above, a group forming, together with the atoms to which it is bonded, an ester group which is hydrolyzable in vivo;
or a salt thereof.

2. The compound of claim 1, wherein said salt is a pharmaceutically acceptable salt.

3. The compound of claim 1, wherein the chiral center

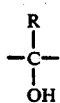

of the phosphinyl side chain of said compound is in the S position.

4. The compound of claim 1, wherein X is —CH$_2$—CH$_2$—, —CH=CH— (cis or trans), —C≡C—, or —CH$_2$O— (where —CH$_2$— is attached to Z).

5. The compound of claim 1, wherein R is hydrogen.

6. The compound of claim 1, wherein at least one of $R^4$ and $R^5$, together with the atoms to which it is bonded, forms a free acid or alkali metal salt group on said compound of the formula I, or which, together with the atoms to which it is bonded, forms a group such that said compound of the formula I is an ester prodrug which is hydrolyzable in vivo.

7. The compound of claim 1, where $R^1$ is aryl and $R^2$ is alkyl.

8. The compound of claim 1, where $R^3$ is aryl.

9. The compound of claim 1, where said compound is selected from:
- (S)-4-[[[4-(4-fluorophenyl)-6-(1-methylethyl)-2-phenyl-5-pyrimidinyl]ethynyl]-methoxyphosphinyl]-3-hydroxybutanoic acid, methyl ester;
- (S)-4-[[[4-(4-fluorophenyl)-6-(1-methylethyl)-2-phenyl-5-pyrimidinyl]-ethynyl]-hydroxyphosphinyl]-3-hydroxybutanoic acid, disodium salt;
- (S)-4-[[2-[4-(4-fluorophenyl)-6-(1-methylethyl)-2-phenyl-5-pyrimidinyl]ethenyl]-methoxyphosphinyl]-3-hydroxybutanoic acid, methyl ester;
- (S)-4-[[2-[4-(4-fluorophenyl)-6-(1-methylethyl)-2-phenyl-5-pyrimidinyl]ethenyl]-hydroxyphosphinyl]-3-hydroxybutanoic acid, disodium salt;
- (S)-4-[[2-[4-(4-fluorophenyl)-6-(1-methylethyl)-2-phenyl-5-pyrimidinyl]ethyl]-methoxyphosphinyl]-3-hydroxybutanoic acid, methyl ester; and
- (S)-4-[2-[4-(4-fluorophenyl)-6-(1-methylethyl)-2-phenyl-5-pyrimidinyl]ethyl]-hydroxyphosphinyl]-3-hydroxybutanoic acid, disodium salt.

10. A method for inhibiting the activity of the enzyme HMG—CoA reductase, comprising the step of contacting a compound of claim 1 with said enzyme.

11. A hypocholesterolemic composition comprising an amount of said compound of claim 1 effective therefor, and a pharmaceutically acceptable vehicle or diluent.

12. A hypolipidemic composition comprising an amount of said compound of claim 1 effective therefor, and a pharmaceutically acceptable vehicle or diluent.

13. An antiatherosclerotic composition comprising an amount of said compound of claim 1 effective therefor, and a pharmaceutically acceptable vehicle or diluent.

14. A hypolipoproteinaemic composition comprising an amount of said compound of claim 1 effective therefor, and a pharmaceutically acceptable vehicle or diluent.

15. A method for the prevention or treatment of hypercholesterolemia, comprising the step of administering to a subject in need thereof a compound of claim 1 in an amount effective therefor.

16. A method for the prevention or treatment of atheroschlerosis, comprising the step of administering to a subject in need thereof a compound of claim 1 in an amount effective therefor.

17. A method for the prevention or treatment of hyperlipidemia, comprising the step of administering to a subject in need thereof a compound of claim 1 in an amount effective therefor.

18. A method for the prevention or treatment of hyperlipoproteinaemia, comprising the step of administering to a subject in need thereof a compound of claim 1 in an amount effective therefor.